US009218452B2

(12) United States Patent
Varna et al.

(10) Patent No.: US 9,218,452 B2
(45) Date of Patent: Dec. 22, 2015

(54) METHOD AND SYSTEM TO AUTOMATICALLY LOAD USER SETTINGS TO WIRELESS ULTRASOUND PROBE

(75) Inventors: Srinivas K Varna, Bangalore (IN); Mark Steven Urness, Wauwatosa, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 212 days.

(21) Appl. No.: 13/327,906

(22) Filed: Dec. 16, 2011

(65) Prior Publication Data

US 2013/0158397 A1  Jun. 20, 2013

(30) Foreign Application Priority Data

Dec. 27, 2010  (IN) .............................. 3964/CHE/2010

(51) Int. Cl.
*G06K 9/00* (2006.01)
*G06F 19/00* (2011.01)
*A61B 8/00* (2006.01)

(52) U.S. Cl.
CPC ............ *G06F 19/322* (2013.01); *A61B 8/4472* (2013.01); *A61B 8/565* (2013.01); *A61B 8/585* (2013.01); *G06F 19/321* (2013.01); *G06F 19/3412* (2013.01); *A61B 8/4438* (2013.01)

(58) Field of Classification Search
CPC .......... A61B 6/545; A61B 8/00; G06Q 50/24; G06F 19/321
USPC ........... 600/407, 437, 443, 447, 300; 128/916
See application file for complete search history.

(56) References Cited

U.S. PATENT DOCUMENTS

| 6,773,398 B2 | 8/2004 | Ogasawara et al. |
|---|---|---|
| 2004/0171935 A1 | 9/2004 | Van Creveld et al. |
| 2005/0091680 A1* | 4/2005 | Kondo .............................. 725/12 |
| 2006/0058654 A1 | 3/2006 | Di Marco et al. |
| 2006/0213996 A1* | 9/2006 | Crucs ......................... 235/462.13 |
| 2009/0054768 A1 | 2/2009 | Halmann et al. |
| 2009/0112099 A1 | 4/2009 | Kurokawa |
| 2010/0292575 A1 | 11/2010 | Sharp |
| 2011/0096963 A1* | 4/2011 | Shekhara et al. .............. 382/128 |

FOREIGN PATENT DOCUMENTS

| CN | 1419894 A | 5/2003 |
|---|---|---|
| CN | 101371792 A | 2/2009 |

OTHER PUBLICATIONS

Unofficial English translation of Chinese Office Action issued in connection with corresponding CN Application No. 201110463064.1, on Aug. 5, 2014.

* cited by examiner

*Primary Examiner* — Elmer Chao
(74) *Attorney, Agent, or Firm* — GE Global Patent Operation; Marc A. Vivenzio

(57) ABSTRACT

An ultrasound imaging system is provided, including a beamformer in communication with a transducer probe to acquire ultrasound image data for communication by a transceiver. An identity server can include a series of profiles each including a unique identifier of an external environment and a unique predefined system setting of the system. A tracking system can scan for a first tag having a unique identifier of a user of the system and for a second tag having a unique identifier of the patient. The identity server is operable to select a match of one of the series of profiles based on the acquired unique identifier and automatically communicate the profile to the transceiver for automatic activation of the system settings to the ultrasound imaging system.

20 Claims, 1 Drawing Sheet

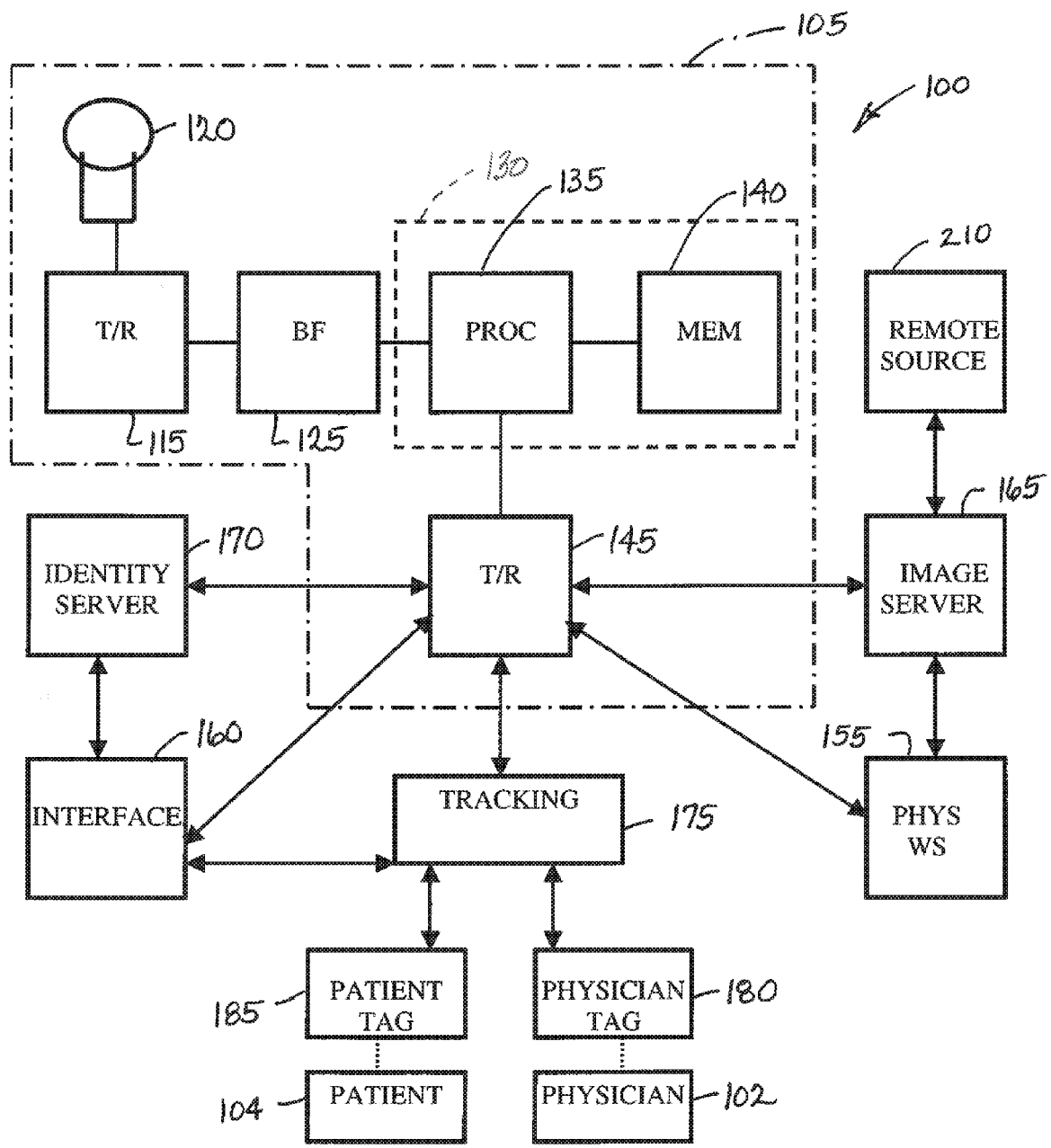

METHOD AND SYSTEM TO AUTOMATICALLY LOAD USER SETTINGS TO WIRELESS ULTRASOUND PROBE

This invention generally relates to a method of and system for setting system parameters to perform an ultrasound imaging procedure, and method thereof.

BACKGROUND

Known ultrasound imaging systems include an image processor used in conjunction with ultrasound beams emitted by a transducer probe to produce an ultrasound image on a display device. The display device presents the ultrasound image while the user interface permits an operator to control the functions, operations, image settings, adjustments to the ultrasound image, and the like.

Typically, the user of the ultrasound imaging systems manually enters information of the type of transducer probe to use and system parameters and unique settings based on the scanned anatomy and size of imaged subject before the user operating the ultrasound imaging system to acquire images of the imaged subject. There is a desire in the field for a technology that can reduce the time to perform this workflow and reduce the number of steps of performing ultrasound image acquisition.

BRIEF DESCRIPTION

The above-mentioned shortcomings, disadvantages and problems are addressed by the embodiments described herein in the following description of a method and system to generate multi-display technology with dedicated software so as to provide separate displays for the physician and the patient (or family), so as to optimally address their specific needs.

In one embodiment, an ultrasound imaging system is provided. The system comprises a beamformer in communication with a transducer probe to acquire ultrasound image data of a patient. A transceiver can be connected to receive transmission of the acquired ultrasound image data, the transceiver in wireless communication to send the ultrasound image data to an interface for illustration. An identity server can be in wireless communication with the transceiver, the identity server including a series of profiles each including a unique identifier of an external environment and a unique predefined system setting of the system. A tracking system is operable to scan for a first tag having a unique identifier of a user of the system and for a second tag having a unique identifier of the patient, the tracking system in wireless communication with the transceiver. The identity server is operable to select a match of the one of the series of profiles to the unique identifier and automatically communicate the profile to the transceiver for automatic activation of the system settings in the profile to the ultrasound imaging system.

In another embodiment, a method to automatically load user settings to an ultrasound imaging system to perform ultrasound image acquisition of a patient, the method comprising communicating acquired ultrasound image data from transducer probe to a beamformer; receiving a transmission of the acquired ultrasound image data at a transceiver, communicating the acquired ultrasound image data in wireless transmission for illustration at an interface; receiving a plurality of profiles each including a unique identifier of an external environment and a unique predefined system setting of the ultrasound imaging system; scanning a defined space for a first tag having a unique identifier of a user of the ultrasound imaging system and for a second tag having a unique identifier of the patient, the tracking system in wireless communication with the transceiver; selecting a match of one of the plurality of profiles to the unique identifier; and automatically communicating the selected profile for wireless transmission to the transceiver for automatic activation of the system settings in the profile to the ultrasound imaging system.

Systems and methods of varying scope are described herein. In addition to the aspects and advantages described in this summary, further aspects and advantages will become apparent by reference to the drawings and with reference to the detailed description that follows.

BRIEF DESCRIPTION OF THE DRAWINGS

FIG. 1 shows a schematic diagram of an embodiment of an ultrasound imaging system having a multiple displays in accordance with the subject matter described herein.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

In this document, the terms "a" or "an" are used, to include one or more than one. In this document, the term "or" is used to refer to a nonexclusive or, unless otherwise indicated.

FIG. 1 illustrates an embodiment of an ultrasound imaging system 100 having a technical effect to provide a user (e.g., the physician or clinician) 102 with a simplified workflow so as to enhance the speed and efficiency in employing ultrasound imaging system to acquire ultrasound imaging data of an imaged subject or patient 104, in accordance to the subject matter described herein.

One embodiment of the ultrasound imaging system 100 can generally include a wireless probe 105 in stand-alone operation to acquire real-time ultrasound imaging data of the patient 104. Generally, the wireless probe 105 can include a transmitter/receiver 115 that drives an array of elements, for example, piezoelectric crystals, within a transducer, transducer probe or probe 120 to emit pulsed ultrasonic signals into a body or volume of the patient 104. A variety probes 120 and geometries transmitting the ultrasound signals from the probe 120 may be used.

The ultrasonic signals are back-scattered from anatomical structures in the patient 104, for example, blood cells or muscular tissue, to produce echoes that return to the elements of the probe 120 and received at the transmitter/receiver 115. The transmitter/receiver 115 communicates detection of the back-scattered ultrasound signals to the beamformer 125. The beamformer 125 generally performs beamforming including translating the echo data detected by the elements of the transducer probe 120 into ultrasound detection signal (e.g., RF). The beamformer 125 provides the ultrasound detection signal to a controller 130.

An embodiment of the controller 130 can generally include a processor 135 in communication with a memory 140 operable to process and translate the ultrasound detection signal (e.g. RF signal or IQ data pairs) into a general real-time ultrasound image data for illustration. The processor 135 can be in communication to execute computer-readable program instructions stored in the memory 140 to perform translation of the ultrasound detection signal into an ultrasound image data for illustration. The processor 135 can be instructed to perform one or more processing operations according to a plurality of selectable ultrasound modalities on the acquired ultrasound detection information. Acquired ultrasound detection information may be processed in real-time during a scanning session as the echo signals are received. Additionally or alternatively, the ultrasound detection information may be stored temporarily in the memory 140 during a scanning session and processed in less than real-time in a live or off-line operation. The acquired ultrasound detection data or information or signal not scheduled to for display can immediately be stored to the memory 140. The memory 140 may comprise various types of computer readable mediums (e.g., memory stick, hard-drive, disk, CD, DVD, or other conventional storage medium or combination thereof).

The wireless probe 105 can further include a wireless transceiver 145 operable to transmit or receive wireless communications of probe scanning settings, patient or user identifiers, or other data that will be discussed in more detail below.

The ultrasound imaging system 100 can further include a physician workstation 155, an interface 160, an image server 165, an identifier server 170, and a tracking system 175 in wireless communication with the wireless probe 105.

Embodiments of the physician workstation 155 can include a stand-alone computer (e.g., desktop or laptop, blackberry, etc) or can include various arrangements or combinations thereof in wireless communication with the wireless probe 105.

The interface 160 can be operable to receive wireless communications of acquired ultrasound image data from the wireless probe 105 for illustration or visualization on the interface 160. In addition to illustrating acquired ultrasound image data of the patient 104, the interface 160 can provide visualization and interaction with the user 102, and provide certain control operations and be configured to receive inputs from the user 102 of the system 100 for wireless communication to the wireless probe 105. An embodiment of the interface 160 can include one or more monitors that present a graphic display of patient information, including diagnostic ultrasound images to the user 102 for review, measurement, diagnosis and analysis. At least a portion of the interface 160 can include a user selectable element with touch sensitive portion or touch sensitive technology to receive input from the user 102. The interface 160 may automatically display the generated ultrasound image data in various formats as output from the processor 135, for example, planes from two-dimensional (2D) and/or three-dimensional (3D) ultrasound data either in real-time or from stored 2D or 3D data-sets of ultrasound detection or image data in the memory 140. The processing of the ultrasound detection or image data by the processor 135 can be based in part on user inputs, for example, user selections received at the user interface 160. The interface 160 may further include input devices such as a keyboard, a touch-screen, a keypad, a joystick, dials, or other conventional input device or combination thereof operable to receive data from the user or clinician for communication to the processor 135 or memory 140.

The interface 160 can also be connected in communication to receive input data or image data from another source 210 (e.g., magnetic resonance imager, x-ray scanner, etc.) via the image server 165 for combination with the illustration of ultrasound image data at the interface 160. The interface 160 can also include output devices such as LCD or LED monitors, hand-held display, CRT projector, personal data assistant (RDA), LEDs lights, touch-screens, alarm devices, etc. Examples of touch-screen technology that can be provided on the interface 160 can include but is not limited to touch sensitive elements such as capacitive sensors, membrane switches, and infrared detectors.

The image server 165 is connected in wireless communication with the wireless probe 105 to receive acquired image data for storage in the image server 165. The image server 165 can be connected via a network connection to communicate the acquired image data to remote devices for viewing or view image data stored in the local memory 140 of the wireless probe 105. An example of the image server 165 can be a picture archival system (PACS). The image server 165 can also be connected to receive image data for combination with the acquired image stored at the image server 165 or at the local memory 140 for illustration at the interface 160.

The identity server 170 can be in wireless communication with the probe 105. An embodiment of the identity server 170 can include storage of a profile associated with multiple users of the probe 105. The profile can include an identifier of the user, scanner settings for operation of the wireless probe 105 predefined by the user or stored based on the scanner settings when last employed by the user, and a predefined manner to store the acquired image data at the memory or wirelessly communicate the acquired image data for real-time illustration at the interface 160 or store at the image server 165 or combination thereof. In one embodiment, the wireless probe 105 is operable to query the identity server 170 to search and recall the profile based on input of the identifier of the user. The identity server 170 can automatically wirelessly communicated the profile to the wireless probe 105 for automatic activation at the scanner settings of the profile. If no profile is found for the identifier of the user, the identity server 170 can be automatically configured to wirelessly communicate a general profile including scanner settings for activation at the wireless probe 105.

The tracking system 175 can include an identifier tag 180 for the physician and an identifier tag 185 for the patient 104. The tracking system 175 can use various transmission mediums (e.g., optical, radio frequency (rf), infrared (ir), etc.) to communicate with or detect the identifier tags 180, 185, and then translate unique identifier data associated with the user or patient attached to the respective tags 180, 185, respectively.

In one embodiment, the tracking system 175 can detect and identify the identifier associated with the user 102 associated with the tag 180, and in response automatically communicate the identifier to the wireless probe 105. In response to receiving the identifier data, the wireless probe 105 can automatically query the identifier server 170 to search for the profile including scanner settings for the identifier data, and automatically communicated the profile including scanner settings for activation at the wireless probe 105 to perform image acquisition of the patient 104.

The tracking system 175 can also be configured to automatically detect a patient identifier associated with the patient tag 185 at the patient 104, and automatically generate a wireless communication of the patient identifier to the wireless probe 105. In response, the wireless probe 105 can automatically associate the patient identifier with the acquired image data for the respective patient for storage at the memory 140 or wireless communication to the interface 160 or image server 165.

Having described a general construction of the embodiment of the ultrasound imaging system 100, the following is a general description of the operation and technical effect of an embodiment of the ultrasound imaging system 100 described above. Although the operation is described in accordance to the following acts, it should be understood that the sequence of the acts can vary. Also, it should be understood that the following description of acts of the method is not limiting, and that one or more of the described acts may not be needed.

Assume initially the user 102 is operable to pre-program the identity server 170 via the interface 160 with multiple preprogrammed profiles of system settings and visual arrangements of the acquired ultrasound image data for each of a series of users 102 of the wireless probe 105. Each of the preprogrammed profiles can be stored with an identifier either assigned by the user and/or the controller 130. In one example, one or more of the multiple pre-programmed settings and arrangements of the acquired image data is stored with an identifier of a certain medical or imaging procedure (e.g., fetal ultrasound, etc.). In yet another example, the user can create one or more of the multiple pre-programmed profiles stored with the user identifier indicative of the user to execute the medical or imaging procedure with the wireless probe 105. According to one embodiment, each profile can be pre-staged for known environments with the physical components/hardware or probe 120 of the system 100 or identifiers of the user 102 in the defined space. Each profile can be stored on the local memory 140 of the wireless probe 105 or at the identity server 170 or both. Each profile can include configuration or predefined settings for the ultrasound system 100, including a refresh rate, type or identification of one of a plurality of probes 120, image resolutions, contrast level of the acquired image data for illustration at the interface 170, type of information or processing of ultrasound image data for illustration at each of a series of interfaces 160 or display fields. Example identifiers can include textual references for name of a predefined space in a healthcare facility (e.g., exam room, operating room, etc.) or if stand alone system 100.

The method of operation of the system 100 includes the tracking system 175 detecting and identifying the user identifier associated with the user tag 180 or the patient identifier associated with the patient tag 185. The tracking system 175 can also scan a defined area or space to detect or identify other hardware devices, number and type of interfaces 160, identification of interchangeable probes 120, etc. Upon completing the scan of the defined space, the tracking system 175 can automatically create a wireless communication of the user identifier and patient identifier, and identification of hardware or interfaces 160 to the wireless probe 105.

In response, the wireless probe 105 can automatically query the identity server 170 to search, find a match and recall a selection from a multiple number of pre-programmed profiles that is particularly associated with the user identifier or imaging procedure schedule for the respective patient identifier. A match can be performed based on a textual search of key terms or identifiers stored with each profile. If a match is executed or made, the identity server 170 can automatically wirelessly communicate the selection of the profile to the wireless probe 105 for activation to perform the image acquisition on the patient 104. The identity server 170 may communicate the selected profile for illustration at the interface 160 to prompt an instruction of confirmation from the user or operator 102. Also, the user 102 can selectively adjust the selected preprogrammed profile or the system settings at the wireless probe 105 in real-time via the interface 160. If no profile match is made by the identity server 170, the identity server 170 can communicate the list of detected hardware or identifiers, a recommended configuration based on a predefined profile of general settings, and a prompt to the user 102 to receive a user instruction to save or store the recommended predefined profile with general settings for the detected identifiers communicated from the tracking system 175 for future reference.

The interface 160 can be operable to include graphic illustrations of prompts to receive instructions from the user to confirm activation or to instruct de-activation of any profile for storage at the identity server 170 or for implementation at the wireless probe 105 to provide control for specific situations to the user 102.

Upon completion of the medical or imaging procedure, the controller 130 is operable to receive instructions via wireless communication from the interface 160 with another identifier associated with another user or pre-programmed transmission/storage of the acquired image data. For example, the other identifier can be indicative of a new user (e.g., physician or technician). In another example, the wireless probe 105 can automatically detect that one or more of the multiple interfaces 160 can be disconnected and/or one or more additional interfaces 160 can be connected in association with performing a different medical procedure, and communicated this information to the identity server 170 which may automatically trigger searching and recalling a new profile for automatic wireless communication to and activation of the wireless probe 105. In still yet another example, the user 102 via the interface 160 can select another one of the pre-programmed profiles based on an identifier (e.g., one or more alphanumeric symbols, etc.) representative of a step of another medical procedure.

A technical effect of the above described ultrasound imaging system 100 and method of operation can be to provide automatic configuration of the system 100 based on the external environment (user 102 (e.g., doctor, nurse, or other user) or patient 104) or hardware or other physical components that would affect the scanning settings of the ultrasound imaging system 100, allowing ready movement of the system 100 to various locations where the ultrasound imaging can be performed. The system 100 can configure itself automatically, and can be ready for image acquisition promptly after startup at the location to be use. The system 100 can be operated at multiple locations because of the automatic configuration of the system settings, allowing the system 100 to be employed more often and reducing the need for multiple systems 100. The system 100 as described can also allow user 102 more flexibility in the design of the multiple defined spaces where the system 100 can be employed, and can allow use of the system 100 in more predefined spaces where extensive setup may otherwise discourage use. The wireless probe 105 also enhances handling by the user 102 in image acquisition, and reduces complexity of use of the system 100 because activation of the system settings can be performed automatically performed by the system 100 ready for image acquisition.

In various embodiments of the subject matter described herein, the method can be implemented in software, hardware, or a combination thereof. The method provided by various embodiments described herein, for example, can be implemented in software by using standard programming languages such as, for example, C, C++, Java, and the like. As used herein, the terms "software" and "firmware" are interchangeable, and include any computer program instructions stored in memory for execution by a computer, including RAM memory, ROM memory, EPROM memory, EEPROM memory, and non-volatile RAM (NVRAM) memory. The above memory types are exemplary only, and are thus limiting as to the types of memory usable for storage of a computer program.

The set of program instructions may include various commands that instruct the processor to perform specific operations such as the processes of the various embodiments of the invention. The set of program instructions may be in the form of a software or software program. The software may be in various forms such as system software or application software. Further, the software may be in the form of a collection of separate programs, a program module within a larger program or a portion of a program module. The software also may include modular programming in the form of object-oriented programming. The processing of input data by the processor may be in response to user commands, or in response to results of previous processing, or in response to a request made by another processor.

The processor 135 executes a set of instructions (e.g., corresponding to the method steps described herein) that are stored in one or more storage elements (also referred to as computer usable medium) of the memory 140. The memory 140 may be in the form of a database or a physical memory element present in the processor 135. The memory 140 may also hold data or other information as desired or needed. The memory 140 can be, for example, but not limited to, an electronic, magnetic, optical, electromagnetic, infrared, or semiconductor system, apparatus, device, or propagation medium. More specific examples of the memory 140 include, but are not limited to, the following: a random access memory (RAM) a read-only memory (ROM), an erasable programmable read-only memory (EPROM or Flash memory), a Hard Disc Drive (HDD) and a compact disc read-only memory (CDROM).

This written description uses examples to disclose the subject matter, including the best mode, and also to enable any person skilled in the art to make and use the subject matter. The subject matter may include other examples that occur to those skilled in the art. Such other examples are intended to be within the scope of the subject matter if they have structural elements that do not differ from the literal language of the subject matter described herein, or if they include equivalent structural elements with insubstantial differences from the literal languages of the subject matter.

What is claimed is:

1. An ultrasound imaging system configured to be operated by a user for executing a medical or imaging procedure on a patient, the system comprising:
    a beamformer in communication with a transducer probe to acquire ultrasound image data of the patient;
    a transceiver connected to receive transmission of the acquired ultrasound image data, the transceiver in wireless communication to send the ultrasound image data to an interface for illustration;
    an identity server in wireless communication with the transceiver, the identity server including a plurality of profiles each including a unique identifier of an external environment and a unique predefined system setting of the system; and
    a tracking system configured to scan for and detect a first tag having a unique identifier, the unique identifier of the first tag identifying the user of the system and to scan for and detect a second tag having a unique identifier, the unique identifier of second tag identifying the patient, the tracking system in wireless communication with the transceiver, wherein the identity server is configured to select a match of the one of the plurality of profiles based on the detected unique identifier of the user and automatically communicate the selected profile of the user to the transceiver for automatic activation of the unique predefined system setting for executing the medical or imaging procedure using the ultrasound imaging system and associating acquired image data of the patient with the unique identifier of the second tag when storing the acquired image data.

2. The ultrasound imaging system of claim 1, further comprising an imager server in wireless communication to receive the ultrasound image data from the transceiver for storage at the image server.

3. The ultrasound imaging system of claim 1, further comprising a local memory in communication with a processor the processor connected to communicate the ultrasound image data from the beamformer to the transceiver.

4. The ultrasound imaging system of claim 1, wherein the profile includes settings from the group consisting of a refresh rate, at type of probe, a unique identifier of the probe, image resolutions of the acquired image data for illustration at the interface, contrast level of the acquired image data for illustration at the interface.

5. The ultrasound imaging system of claim 1, wherein the tracking system includes a transmission technology to communicate with or detect the first tag and the second tag and translate unique identifier data associated with the user or the patient attached to the respective tags, the transmission technology selected from the group consisting of: optical, radio frequency (rf) infrared (ir), and bar code recognition.

6. The ultrasound imaging system of claim 1, wherein the unique identifier of the external environment includes the second tag.

7. The ultrasound imaging system of claim 1, wherein the unique identifier of the external environment includes a tag having a unique identifier associated with a user of the system.

8. The ultrasound imaging system of claim 1, wherein the interface is configured to prompt the user for a confirmation of the profile selected by the identity server.

9. The ultrasound imaging system of claim 8, wherein if the identity server cannot find a match of the profile to the unique identifier communicated from the tracking system, the identity server is configured to automatically communicate a default profile of system settings via wireless transmission to the transceiver for activation of image acquisition by the system.

10. A method to automatically load settings to an ultrasound imaging system corresponding to an operator of the ultrasound imaging system to perform ultrasound image acquisition of a patient, the method comprising:
    communicating acquired ultrasound image data from a transducer probe to a beamformer;
    receiving a transmission of the acquired ultrasound image data at a transceiver, communicating the acquired ultrasound image data in wireless transmission for illustration at an interface;
    receiving a plurality of profiles each including a unique identifier of an external environment and a unique predefined system setting of the ultrasound imaging system;
    scanning a defined space for a first tag having a unique identifier of the user of the ultrasound imaging system and for a second tag having a unique identifier of the patient, the tracking system in wireless communication with the transceiver;
    selecting a match of one of the plurality of profiles to the unique identifier of the user;
    automatically communicating the selected profile for wireless transmission to the transceiver for automatic activation of the system settings in the profile to the ultrasound imaging system; and associating the acquired ultrasound image data with the unique identifier of the patient determined from the second tag.

11. The method of claim 10, further comprising receiving wireless communication of the acquired ultrasound image data to an image server.

12. The method of claim 10, further comprising communicating the acquired ultrasound image from the beamformer to a processor in communication with a memory, and communicating the acquired ultrasound image data from the processor to the transceiver.

13. The method of claim 10, wherein the profile includes settings from the group consisting of a refresh rate, at type of probe, a unique identifier of the probe, image resolutions of the acquired image data for illustration at the interface, contrast level of the acquired image data for illustration at the interface.

14. The method of claim 10, wherein the tracking system includes a transmission technology to communicate with or detect the first tag and the second tag and translate unique identifier data associated with the user or the patient attached to the respective tags, the transmission technology selected from the group consisting of: optical, radio frequency (rf), infrared (ir), and bar code recognition.

15. The method of claim 10, wherein the unique identifier of the external environment includes the tag having the unique identifier associated with the patient.

16. The ultrasound imaging system of claim 1, wherein the profile is automatically communicated to the transceiver for automatic activation of an imaging procedure schedule in the ultrasound imaging system for acquiring the ultrasound image data from the patient.

17. The ultrasound imaging system of claim 16, comprising a plurality of interfaces for displaying the acquired ultrasound image data, and wherein the identify server is configured to identify an interface associated with the imaging procedure schedule and activate the interface for displaying the ultrasound image data from the patient.

18. The ultrasound imaging system of claim 1, comprising an image server for storing the acquired ultrasound image date according to a data storage profile associated with the unique identifier of the user of the system.

19. The method of claim 10, comprising:
generating an imaging procedure schedule in the ultrasound imaging system, the imaging procedure schedule being determined by the profile associated with the unique identifier of the user;
identifying an interface for illustrating the acquired imaging data from the imaging procedure schedule; and
activating the interface responsive to the image procedure schedule determined by the profile.

20. The method of claim 10, comprising;
scanning the defined space to identify hardware devices of the ultrasound imaging system;
communicate an identification of the identified hardware devices to the transceiver; and
identify a pre-programmed profile associated with the user profile and the identified hardware devices to determine an imaging procedure schedule for performing ultrasound image acquisition associated with the unique identifier.

* * * * *

UNITED STATES PATENT AND TRADEMARK OFFICE
CERTIFICATE OF CORRECTION

| | | |
|---|---|---|
| PATENT NO. | : 9,218,452 B2 | Page 1 of 1 |
| APPLICATION NO. | : 13/327906 | |
| DATED | : December 22, 2015 | |
| INVENTOR(S) | : Varna et al. | |

It is certified that error appears in the above-identified patent and that said Letters Patent is hereby corrected as shown below:

On the Title Page, in item (75), under "Inventors", in Column 1, Line 1, delete "Srinivas K Varna," and insert -- Srinivas K. Varna, --, therefor.

In the Specification

In Column 3, Line 30, delete "etc)" and insert -- etc.) --, therefor.

In Column 4, Line 2, delete "(RDA)," and insert -- (PDA), --, therefor.

In Column 5, Line 31, delete "interface 170," and insert -- interface 160, --, therefor.

In the Claims

In Column 8, Line 25, in Claim 5, delete "(rf)" and insert -- (rf), --, therefor.

In Column 10, Line 21, in Claim 20, delete "comprising;" and insert -- comprising: --, therefor.

Signed and Sealed this
Sixteenth Day of August, 2016

Michelle K. Lee
*Director of the United States Patent and Trademark Office*